United States Patent
Wright et al.

(10) Patent No.: US 8,460,392 B2
(45) Date of Patent: Jun. 11, 2013

(54) KNEE PROSTHESIS HAVING CROSS-COMPATIBLE DOME AND ANATOMIC PATELLA COMPONENTS

(75) Inventors: Abraham P. Wright, Winona Lake, IN (US); Charles D. Christie, Warsaw, IN (US)

(73) Assignee: DePuy (Ireland) (IE)

(*) Notice: Subject to any disclaimer, the term of this patent is extended or adjusted under 35 U.S.C. 154(b) by 111 days.

(21) Appl. No.: 12/981,946

(22) Filed: Dec. 30, 2010

(65) Prior Publication Data
US 2012/0172994 A1 Jul. 5, 2012

(51) Int. Cl.
*A61F 2/38* (2006.01)
(52) U.S. Cl.
USPC .................. 623/20.18; 623/20.2
(58) Field of Classification Search
USPC ............... 623/20.14–20.36
IPC ............ A61F 2/38
See application file for complete search history.

(56) References Cited

U.S. PATENT DOCUMENTS

| 5,133,758 | A | 7/1992 | Hollister |
| 6,802,864 | B2* | 10/2004 | Tornier ............ 623/20.18 |
| 2004/0143336 | A1* | 7/2004 | Burkinshaw ...... 623/20.15 |

FOREIGN PATENT DOCUMENTS

GB  2433698 A  7/2007

OTHER PUBLICATIONS

European Search Report, European Patent Application No. 12198396.9-1654, Feb. 20, 2013, 9 pages.

* cited by examiner

*Primary Examiner* — David Isabella
*Assistant Examiner* — Yashita Sharma
(74) *Attorney, Agent, or Firm* — Barnes & Thornburg LLP

(57) ABSTRACT

An orthopaedic implant assembly includes a plurality of dome patella components and a plurality of anatomic patella components. Each of the dome patella components and the anatomic patella components is interchangeable with a plurality of femoral components.

8 Claims, 6 Drawing Sheets

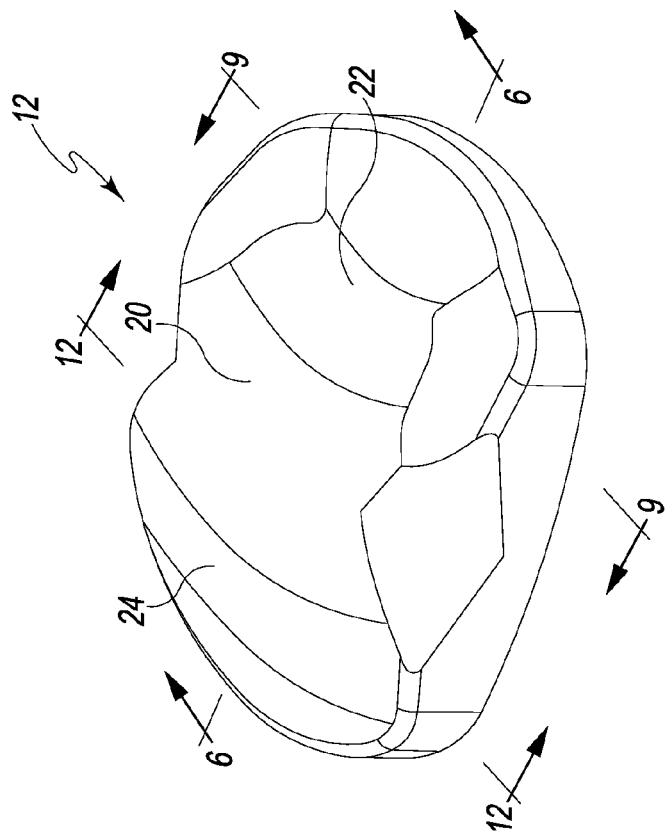
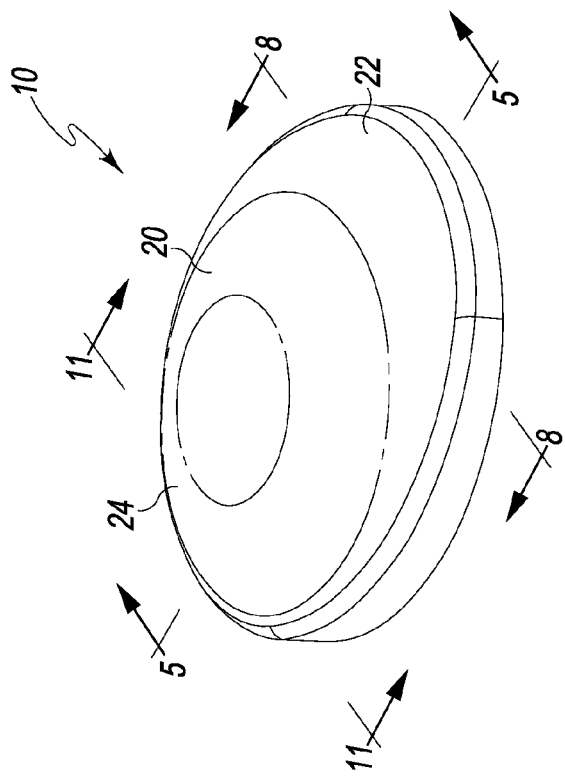
Fig. 1
Fig. 2

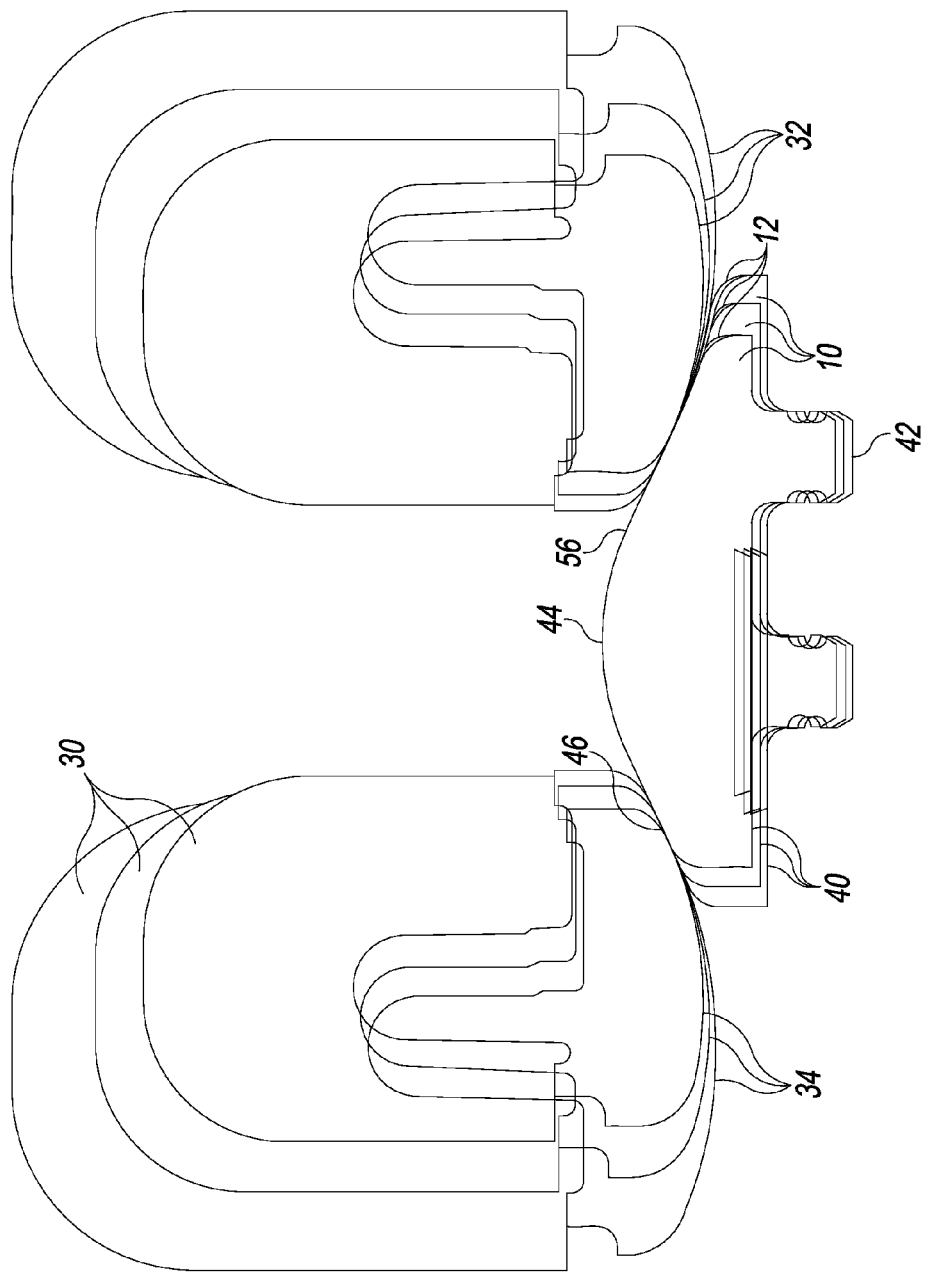

KNEE PROSTHESIS HAVING CROSS-COMPATIBLE DOME AND ANATOMIC PATELLA COMPONENTS

TECHNICAL FIELD

The present disclosure relates generally to an implantable orthopaedic prosthesis, and more particularly to an implantable orthopaedic prosthesis having cross-compatible dome and anatomic patella components.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a patella replacement procedure, a orthopaedic prosthesis is implanted into the patient's patella. Specifically, a prosthetic patella component is secured to the patient's natural patella such that its posterior surface articulates with a femoral component during extension and flexion of the knee.

A conventional dome patella component is embodied as a dome-shaped polymer bearing. Other types of patella components include conforming or anatomic bearings which are designed to conform with the bearing surfaces of the femur. Dome patella components allow for greater movement between the patella component and the femoral component of the knee prosthesis, whereas anatomic patella components are more constrained relative to the femoral component.

Both types of patella components have clinical benefits to fit the needs of a given surgical procedure. However, each type of component is generally matched to a specific type of femoral component. In other words, because of the bearing profile of each type of component, they are generally not cross-compatible with a given design of a femoral component.

SUMMARY

According to one aspect, an implantable orthopaedic knee prosthesis assembly includes a femoral component having medial condyle surface and a lateral condyle surface. The assembly also includes a dome patella component having a posterior bearing surface. The posterior bearing surface of the dome patella component includes a medial articular surface configured to articulate with the medial condyle surface of the femoral component, and a lateral articular surface configured to articulate with the lateral condyle surface of the femoral component. The assembly also includes an anatomic patella component having a posterior bearing surface. The posterior bearing surface of the anatomic patella component includes a medial articular surface configured to articulate with the medial condyle surface of the femoral component, and a lateral articular surface configured to articulate with the lateral condyle surface of the femoral component. When both patella components are viewed in coronal cross sectional views, the medial and lateral articular surfaces of the anatomic patella are congruent with the medial and lateral articular surfaces of the dome patella.

When viewed in a sagittal cross sectional view, the lateral articular surface of the anatomic patella component conforms to the lateral condyle surface of the femoral component. Also, when viewed in such a view, the lateral articular surface of the anatomic patella component defines a concave surface that conforms with a convex surface defined by the lateral condyle surface of the femoral component.

When viewed in a sagittal cross sectional view, the lateral articular surface of the dome patella component is non-conforming with the lateral condyle surface of the femoral component. Further, when viewed in such a view, both the lateral articular surface of the dome patella component and the lateral condyle surface of the femoral component define convex surfaces that are opposed to one another.

When viewed in a sagittal cross sectional view, the medial articular surface of the anatomic patella component is non-conforming with the medial condyle surface of the femoral component. Moreover, when viewed in such a view, both the medial articular surface of the anatomic patella component and the medial condyle surface of the femoral component define convex surfaces that are opposed to one another.

When viewed in a sagittal cross sectional view, the medial articular surface of the dome patella component is non-conforming with the medial condyle surface of the femoral component. Both the medial articular surface of the dome patella component and the medial condyle surface of the femoral component define convex surfaces that are opposed to one another when viewed in such a view.

Each of the patella components may include a monolithic polyethylene body.

According to another aspect, an implantable orthopaedic knee prosthesis assembly includes a femoral component having a medial condyle surface and a lateral condyle surface. The assembly also includes a dome patella component having a posterior bearing surface configured to articulate with the medial condyle surface and the lateral condyle surface of the femoral component. The assembly also includes an anatomic patella component having a posterior bearing surface configured to articulate with the medial condyle surface and the lateral condyle surface of the femoral component. When viewed in a sagittal cross sectional view through the lateral condyle surface of the femoral component, the posterior bearing surface of the anatomic patella component conforms to the lateral condyle surface of the femoral component, and the posterior bearing surface of the dome patella component is non-conforming with the lateral condyle surface of the femoral component. When viewed in a sagittal cross sectional view through the medial condyle surface of the femoral component, the posterior bearing surface of the anatomic patella component is non-conforming with the medial condyle surface of the femoral component, and the posterior bearing surface of the dome patella component is non-conforming with the medial condyle surface of the femoral component.

When both patella components are viewed in coronal cross sectional views, the posterior bearing surface of the dome patella is congruent with the posterior bearing surface of the anatomic patella.

Each of the patella components may include a monolithic polyethylene body.

According to another aspect, an implantable orthopaedic knee prosthesis assembly includes a plurality of femoral components, each of which has a medial condyle surface and a lateral condyle surface. The assembly also includes a plurality of dome patella components configured to be separately positioned in contact with the condyle surfaces of each of the plurality of femoral components. Each of the plurality of dome patella components has a medial/lateral width that is different from at least some of the other of the plurality of dome patella components. Each of the plurality of dome patella components also has a posterior bearing surface having a medial articular surface configured to articulate with the medial condyle surface of each of the plurality femoral components and a lateral articular surface configured to articulate with the lateral condyle surface of each of the plurality of femoral components. The assembly also includes a plurality of anatomic patella components configured to be separately positioned in contact with the condyle surfaces of each of the plurality of femoral components. Each of the plurality of anatomic patella components has a medial/lateral width that is different from at least some of the other of the plurality of anatomic patella components. Each of the plurality of anatomic patella components also has a posterior bearing surface having a medial articular surface configured to articulate with the medial condyle surface of each of the plurality femoral components and a lateral articular surface configured to articulate with the lateral condyle surface of each of the plurality of femoral components.

When viewed in a sagittal cross sectional view, the posterior bearing surface of each of the plurality of anatomic patella components conforms to the lateral condyle surface of each of the plurality of femoral components. The posterior bearing surface of each of the plurality of anatomic patella components defines a concave surface that conforms with a convex surface defined by the lateral condyle surface of each of the plurality of femoral components when viewed in such a view.

When viewed in a sagittal cross sectional view, the posterior bearing surface of each of the plurality of dome patella components is non-conforming with the lateral condyle surface of each of the plurality of femoral components. Both the posterior bearing surface of each of the plurality of dome patella components and the lateral condyle surface of each of the plurality of femoral components define convex surfaces that are opposed to one another when viewed in such a view.

When viewed in a sagittal cross sectional view, the posterior bearing surface of each of the plurality of anatomic patella components is non-conforming with the medial condyle surface of each of the plurality of femoral components. Both the posterior bearing surface of each of the plurality of anatomic patella components and the medial condyle surface of each of the plurality of femoral components define convex surfaces that are opposed to one another when viewed in such a view.

When viewed in a sagittal cross sectional view, the posterior bearing surface of each of the plurality of dome patella components is non-conforming with the medial condyle surface of each of the plurality of the femoral components. Both the posterior bearing surface of each of the plurality of dome patella components and the medial condyle surface of each of the plurality of femoral components define convex surfaces that are opposed to one another when viewed in such a view.

Each of the patella components may include a monolithic polyethylene body.

BRIEF DESCRIPTION OF THE DRAWINGS

The detailed description particularly refers to the following figures, in which:

FIG. 1 is a perspective view of a modified dome patella component of a knee prosthesis;

FIG. 2 is a perspective view of an anatomic patella component of the knee prosthesis;

FIG. 14 is a diagrammatic coronal cross sectional view of a number of differently-sized patella components superimposed upon one another and positioned in contact with a number of differently-sized femoral components that are also superimposed upon one another.

DETAILED DESCRIPTION OF THE DRAWINGS

Figure 4:
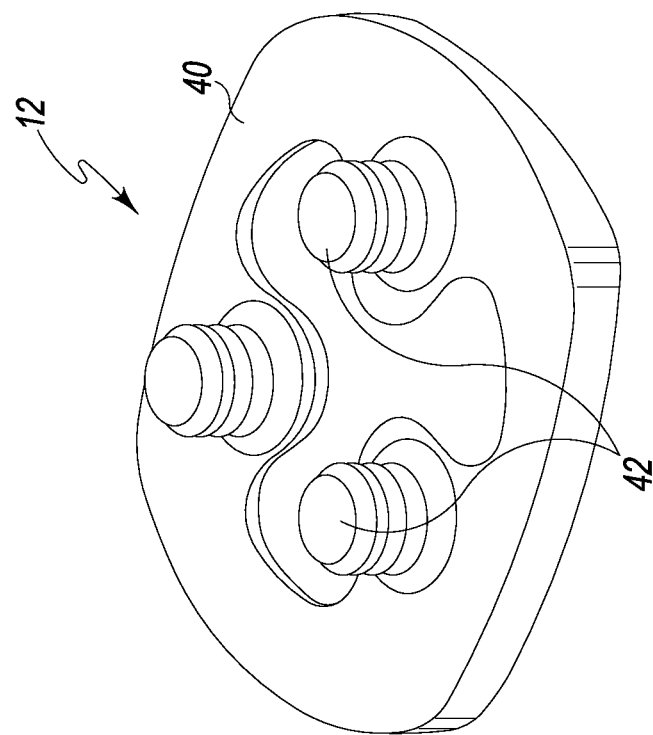
FIG. 4 is a bottom perspective view of the anatomic patella component of FIG. 2.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Figure 7:
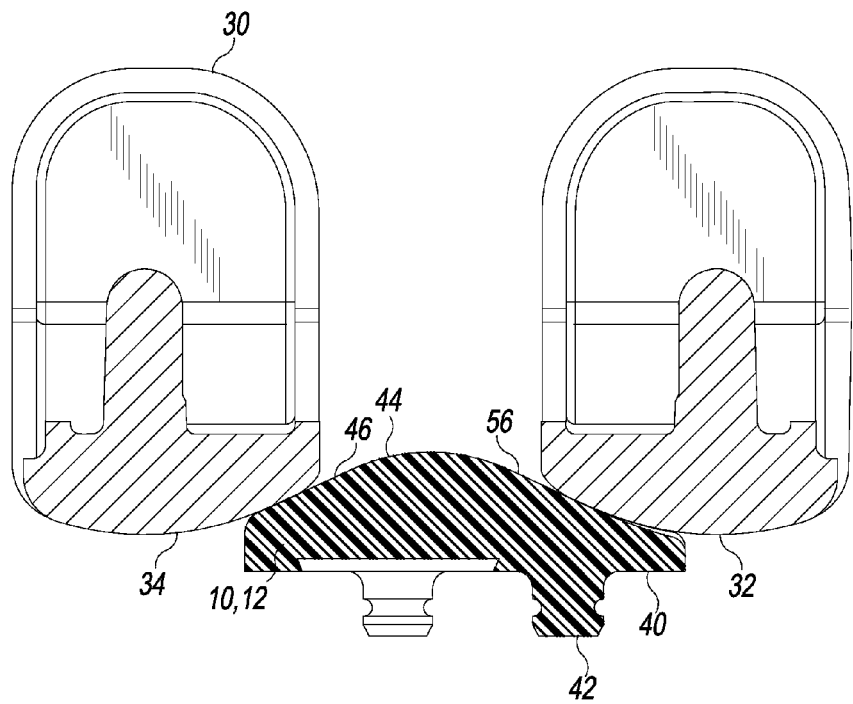
FIG. 7 is a coronal cross sectional view showing the dome patella component of FIG. 5 and the anatomic patella component of FIG. 6 superimposed upon one another and positioned in articular contact with the femoral component of the knee prosthesis.
Figure 10:
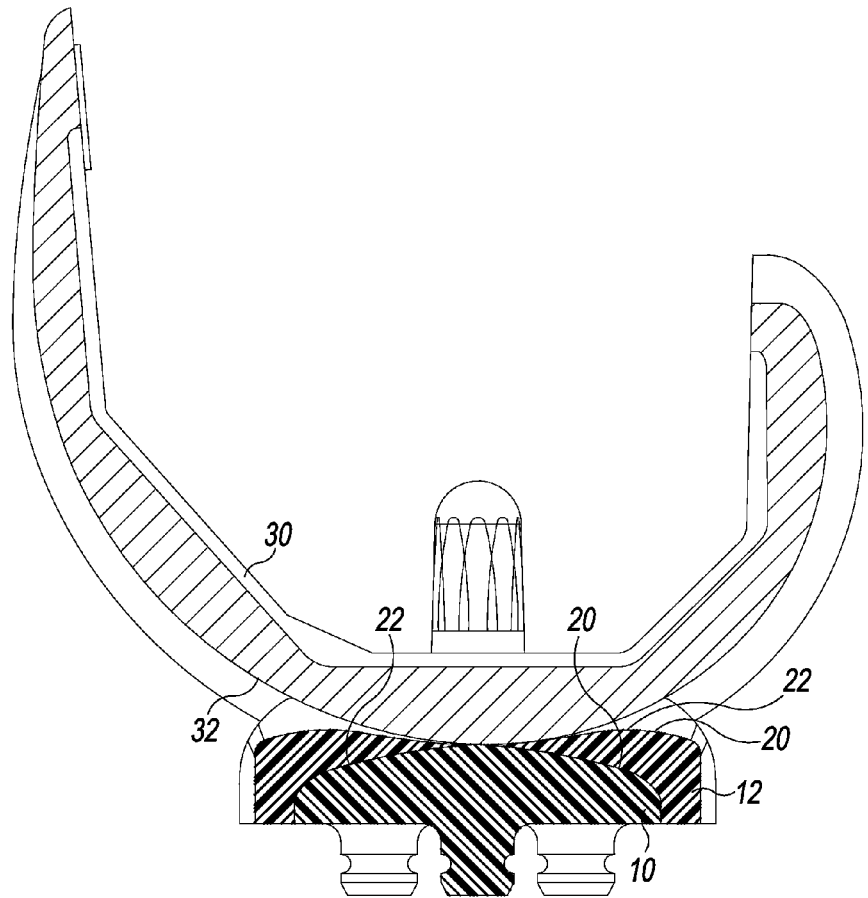
FIG. 10 is a sagittal cross sectional view showing the dome patella component of FIG. 8 and the anatomic patella component of FIG. 9 superimposed upon one another and positioned in articular contact with the femoral component of the knee prosthesis.
Figure 13:
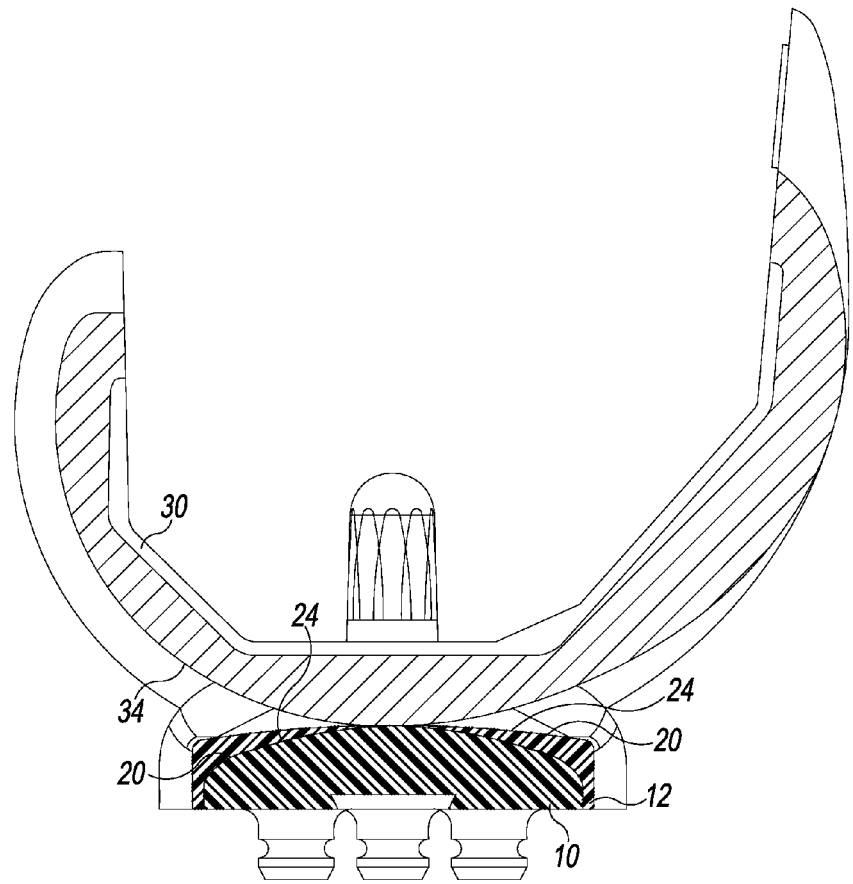
FIG. 13 is a sagittal cross sectional view showing the dome patella component of FIG. 11 and the anatomic patella component of FIG. 12 superimposed upon one another and positioned in articular contact with the femoral component of the knee prosthesis.

Referring now to FIGS. 1-4, there is shown a modified dome patella component 10 and an anatomic patella component 12 of an implantable knee prosthesis. As shown in FIGS. 7, 10, and 13, the knee prosthesis also includes a femoral component 30 that is configured to be secured to a surgically-prepared end of a patient's distal femur (not shown). Both of the patella components 10, 12 include a posterior bearing surface 20 configured to articulate with the condylar surfaces of the femoral component 30. In particular, the posterior bearing surface 20 of the patella components 10, 12 includes a lateral articular surface 22 and a medial articular surface 24. The articular surfaces 22, 24 are configured to articulate with a lateral condyle surface 32 and a medial condyle surface 34, respectively, of the femoral component 30. Specifically, the femoral component 30 is configured to emulate the configuration of the patient's natural femoral condyles, and, as such, the lateral condyle surface 32 and the medial condyle surface 34 are configured (e.g., curved) in a manner which mimics the condyles of the natural femur. The lateral condyle surface 32 and the medial condyle surface 34 are spaced apart from one another thereby defining an intercondylar notch therebetween.

Figure 3:
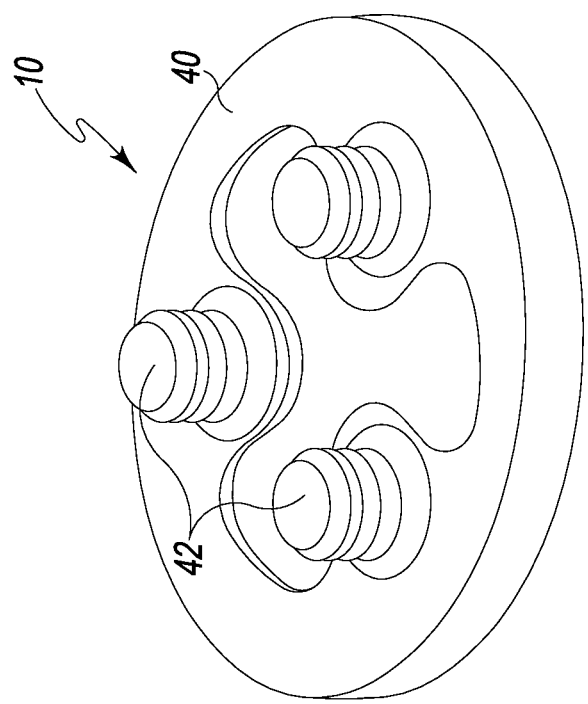
FIG. 3 is a bottom perspective view of the dome patella component of FIG. 1.

As can be seen in FIGS. 3 and 4, the patella components 10, 12 also include a flat anterior surface 40 having a number of fixation members, such as pegs 42, extending away therefrom. The pegs 42 are configured to be implanted into a surgically prepared posterior surface of the patient's natural patella (not shown). In such a way, the posterior bearing surface 20 of the patella components 10, 12 faces toward the femoral component 30 thereby allowing the posterior bearing surface 20 to articulate with the femoral condyle surfaces 32, 34 during flexion and extension of the patient's knee (see, e.g., FIGS. 10 and 13).

Each of the patella components 10, 12 is embodied as a monolithic polymer body constructed with a material that allows for smooth articulation between the patella components 10, 12 and the femoral component 30. One such polymeric material is polyethylene such as ultrahigh molecular weight polyethylene (UHMWPE). The femoral component 30 may be constructed with a biocompatible metal, such as a cobalt chrome alloy, although other materials, such as ceramics, may also be used.

As will be discussed in greater detail, the geometric design of the modified dome patella component 10 and the anatomic patella component 12 allow cross-compatibility with the femoral component 30. In particular, the geometric design of the patella components 10, 12 allow them to be used interchangeably with the femoral component 30. This is in contrast with prior art designs in which a specific design of a femoral component only allowed for use with one type of patella component (i.e., dome or anatomic) or the other, but not both. As will also be discussed, the geometric design of the patella components 10, 12 also allow for the same patella-to-femur sizing rules and the use of a common surgical technique may be used for bone preparation and device implantation.

As shown in FIGS. 3 and 4, the modified dome patella 10 and the anatomic patella 12 have the same fixation features. In particular, the pegs 42 of modified dome patella component 10 and the corresponding pegs 42 of the anatomic component 12 have the same diameter and are arranged in the same pattern (i.e., arranged at the same location) as one another. As such, a common set of instruments and a common surgical technique may be used for bone preparation and device implantation.

Figures 5, 6:
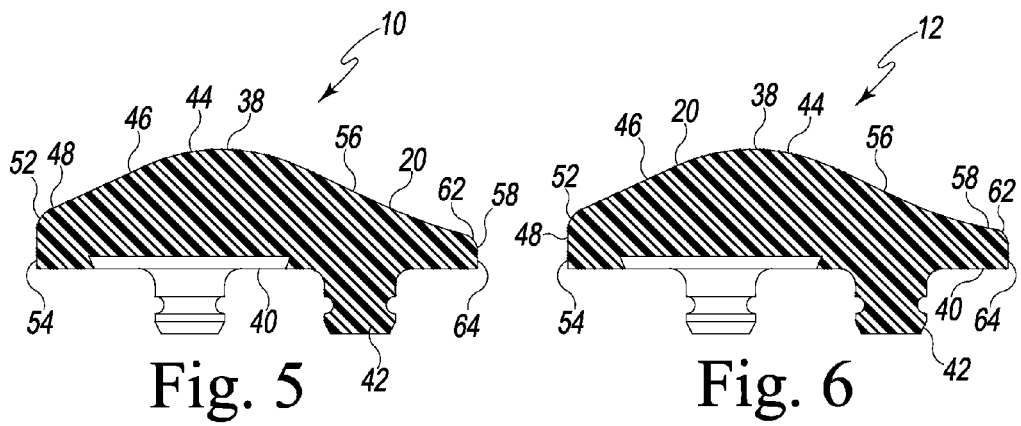
FIG. 5 is a coronal cross sectional view of the dome patella component taken along the line 5-5 of FIG. 1, as viewed in the direction of the arrows.
FIG. 6 is a coronal cross sectional view of the anatomic patella component taken along the line 6-6 of FIG. 2, as viewed in the direction of the arrows.

Referring now to FIGS. 5-7, the patella components 10, 12 and the femoral component 30 are shown in a coronal cross section. As can be seen in FIGS. 1 and 2, by virtue of being distinct component types (dome versus anatomic), the overall geometric shape of the posterior bearing surfaces 20 of the patella components 10, 12 are quite different from one another. However, despite these differences, the posterior bearing surfaces 20 of the patella components 10, 12 are congruent with one another when viewed in coronal cross sectional views such as in FIGS. 5 and 6. In particular, as can be seen in FIGS. 5 and 6, when viewed in a coronal cross sectional view, the posterior bearing surfaces 20 of each of the patella components 10, 12 has a curved peak surface 44. The curved peak surface 44 defines the posterior-most surface of the patella components 10, 12. Specifically, a point on the curved peak surface 44 defines the posterior-most point 38 of the patella components 10, 12. The curved peak surface 44 of both patella components 10, 12 extends medially from the posterior-most point 38 in the general direction toward the anterior surface 40. In particular, as viewed in FIGS. 5 and 6, the curved peak surface 44 transitions to a substantially flat medial surface 46 that extends medially away from the curved peak surface 44. The flat medial surface 46 in turn transitions to a rounded medial edge surface 48 that extends medially away from the flat medial surface 46 in the direction toward the anterior surface 40 of the patella components 10, 12. In the illustrative embodiment of the modified dome patella component 10 and the anatomic patella component 12 described herein, the rounded medial edge surface 48 includes a curved corner surface 52 that transitions from the to the flat medial surface 46 and a flat surface 54 that transitions the curved corner surface 52 to the anterior surface 40 of the patella components 10, 12.

As also shown in FIGS. 5 and 6, the curved peak surface 44 transitions to a substantially flat lateral surface 56 that extends laterally away from the curved peak surface 44. The flat lateral surface 56 in turn transitions to a rounded lateral edge surface 58 that extends laterally away from the flat lateral surface 56 in the direction toward the anterior surface 40 of the patella components 10, 12. The rounded lateral edge surface 58 is embodied as a curved corner surface 62 that transitions from the flat lateral surface 56 and a flat surface 64 that transitions the curved corner surface 62 to the anterior surface 40 of the patella components 10, 12.

As can be seen in FIG. 7, the articular surfaces 22, 24 of the patella components 10, 12 are congruent. Specifically, the lateral and medial articular surfaces 22, 24 formed by the curved peak surface 44, the flat lateral surface 56, and the flat medial surface 46 of both of the patella components 10, 12 are congruent with one another. Such congruency is shown in FIG. 7 in which the profile formed by the surfaces 44, 56, 46 of the dome patella component 10 coincides with the profile formed by the surfaces 44, 56, 46 of the anatomic patella component 12 when the two profiles are superimposed on one another.

Figure 8:
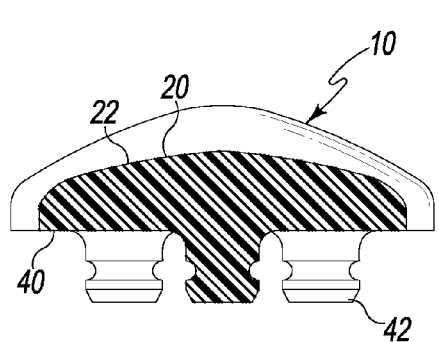
FIG. 8 is a sagittal cross sectional view showing the lateral articular surface of the dome patella component taken along the line 8-8 of FIG. 1, as viewed in the direction of the arrows.
Figure 11:
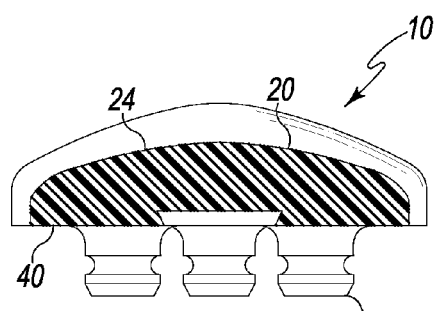
FIG. 11 is a sagittal cross sectional view showing the medial articular surface of the dome patella component taken along the line 11-11 of FIG. 1, as viewed in the direction of the arrows.

As can be seen in FIGS. 1, 8, and 11, the posterior bearing surface 20 of the modified dome patella component 10 defines an axisymmetric, non-conforming articular surface. Specifically, as can be seen in the lateral sagittal cross sectional views of FIG. 10, the lateral articular surface 22 of the posterior bearing surface 20 of the modified dome patella component 10 is non-conforming with the lateral condyle surface 32 of the femoral component 30. Likewise, as can be seen in the medial sagittal cross sectional view of FIG. 13, the medial articular surface 24 of the posterior bearing surface 20 of the modified dome patella component 10 is non-conforming with the medial condyle surface 34 of the femoral component 30. What is meant herein by the term "non-conforming" as it relates to the articular surfaces of one of the patella components 10, 12 relative to the condyle surfaces of the femoral component 30 is that that radius of curvature of the articular surface does not conform—i.e., is not substantially the same as—the radius of curvature of the corresponding condyle surface. For example, as can be seen in the cross sectional view of FIG. 10, the lateral articular surface 22 of the posterior bearing surface 20 of the modified dome patella component 10 is non-conforming with the lateral condyle surface 32 of the femoral component 30 since, amongst other things, the radii of curvature of the surfaces 22, 32 are different in that the surfaces 22, 32 define oppositely-facing convex surfaces. Similarly, as can be seen in the cross sectional view of FIG. 13, the medial articular surface 24 of the posterior bearing surface 20 of the modified dome patella component 10 is non-conforming with the medial condyle surface 34 of the femoral component 30 since, amongst other things, the radii of curvature of the surfaces 24, 34 are different in that the surfaces 24, 34 define oppositely-facing convex surfaces.

Figure 9:
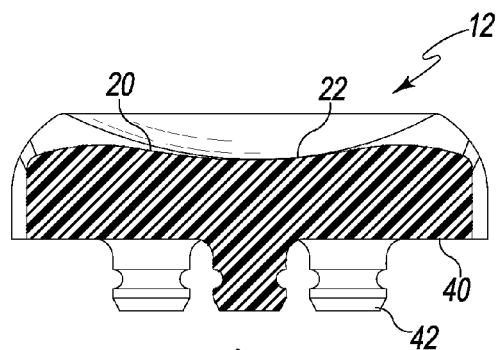
FIG. 9 is a sagittal cross sectional view showing the lateral articular surface of the anatomic patella component taken along the line 9-9 of FIG. 2, as viewed in the direction of the arrows.
Figure 12:
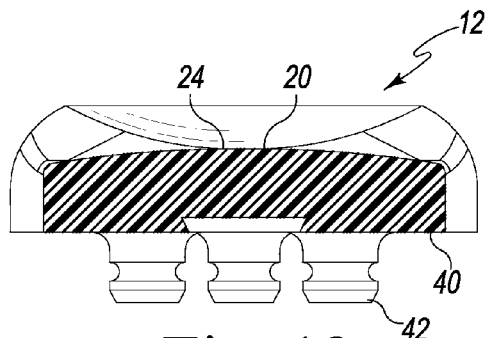
FIG. 12 is a sagittal cross sectional view showing the medial articular surface of the anatomic patella component taken along the line 12-12 of FIG. 2, as viewed in the direction of the arrows.

As can be seen in FIGS. 2, 9, and 12, the posterior bearing surface 20 of the anatomic patella component 12 defines an articular surface that, like the dome patella component 10, is non-conforming on its medial side, but, unlike the dome patella component 10, the lateral side of the articular surface of the anatomic component 12 is conforming. Specifically, as can be seen in the medial cross sectional view of FIG. 13, the medial articular surface 24 of the anatomic patella component 12 is non-conforming with the medial condyle surface 34 of the femoral component 30 in a similar manner as the medial articular surface 24 of the dome patella component 10. However, as can be seen in the lateral cross sectional views of FIG. 10, the lateral articular surface 22 of the of the anatomic patella component 12 conforms with the lateral condyle surface 32 of the femoral component 30. What is meant herein by the term "conforms" as it relates to the articular surfaces of one of the patella components relative to the condyle surfaces of the femoral component is that the radius of curvature of the concave articular surface is substantially the same or somewhat larger than the radius of curvature of the corresponding convex condyle surface. For example, in the case of the lateral articular surface 22 of the anatomic patella component 12 (as shown in the sagittal cross sectional view of FIG. 10), the lateral articular surface 22 conforms with the lateral condyle surface 32 of the femoral component 30 since lateral articular surface 22 defines a concave surface having a similar, but somewhat larger, radius of curvature than the convex surface defined by the lateral condyle surface 32. Such an arrangement creates area contact as opposed to the line contact created in the case of non-conforming surfaces. In one exemplary embodiment, the lateral articular surface 22 has a radius of curvature that is 0-50% larger than the radius of the convex surface defined by the lateral condyle surface 32. In another exemplary embodiment, the lateral articular surface 22 has a radius of curvature that is 10-50% larger than the radius of the convex surface defined by the lateral condyle surface 32. In yet another exemplary embodiment, the lateral articular surface 22 has a radius of curvature that is 30-50% larger than the radius of the convex surface defined by the lateral condyle surface 32. It should be appreciated that the size of the anatomic patella component 12 selected by the surgeon and the varying radii along the surface of the lateral condyle surface 32 may alter the ratio of the radii of curvature of the two surfaces 22, 32 relative to one another at any given location.

A given design of a knee prosthesis is typically made commercially available in a variety of different sizes, particularly in a variety of different widths. This is done to accommodate the many variations in patient size and anatomy across a population. However, the configuration of the knee prosthesis of the present disclosure allows for a high degree of flexibility in regard to the sizing of the femoral component 30 and the patella components 10, 12. In particular, FIG. 14 is a diagrammatic representation of a plurality of differently-sized femoral components 30 (small, medium, and large size) and patella components 10, 12 (small and large size of each type) superimposed upon one another. As can be seen, despite each of the individual femoral components 30 and patella components 10, 12 having a size (e.g., width) that is different from the other femoral components 30 of the group, the basic configuration of the articular surfaces of the patella components 10, 12 remains the same across the range of differently-sized components 10, 12, 30. Specifically, the portion of the lateral and medial articular surfaces 22, 24 formed by the flat lateral surface 56, and the flat medial surface 46, respectively, of both of the patella components 10, 12 are located in the same location throughout the various sizes of patella components 10, 12. Likewise, the inner surfaces of the lateral condyle surface 32 and the medial condyle surface 34 of the femoral component 30 are located in the same location through the various sizes of femoral components 30 such that they articulate with the commonly-located lateral and medial articular surfaces 22, 24 of the patella components 10, 12 across the range of differently-sized femoral components 30 and patella components 10, 12.

It should be appreciated from the above-discussion that the general configuration of the inner surfaces of the lateral condyle surface 32 and the medial condyle surface 34 of the femoral component 30 is the same across the range of differently-sized femoral components 30. Likewise, the general configuration of the portion of the lateral and medial articular surfaces 22, 24 formed by the flat lateral surface 56, and the flat medial surface 46, respectively, of both the domed patella component 10 and the anatomic patella component 12 are the same across the range of differently-sized patella components 10, 12. As such, any size femoral component 30 may be used in conjunction with any size or type of patella component 10, 12 (i.e., any size of dome patella component 10 or any size of anatomic patella component 12). This provides the orthopaedic surgeon with greater flexibility of matching the knee prosthesis to a particular patient's anatomy.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. An implantable orthopaedic knee prosthesis assembly, comprising:

a femoral component having medial condyle surface and a lateral condyle surface, a dome patella component having a posterior bearing surface comprising (i) a medial articular surface configured to articulate with the medial condyle surface of the femoral component, and (ii) a lateral articular surface configured to articulate with the lateral condyle surface of the femoral component, and an anatomic patella component having a posterior bearing surface comprising (i) a medial articular surface configured to articulate with the medial condyle surface of the femoral component, and (ii) a lateral articular surface configured to articulate with the lateral condyle surface of the femoral component, wherein, when both patella components are viewed in coronal cross sectional views, the medial and lateral articular surfaces of the anatomic patella component are congruent with the medial and lateral articular surfaces of the dome patella component; wherein, when viewed in a sagittal cross sectional view, the lateral articular surface of the anatomic patella component conforms to the lateral condyle surface of the femoral component; and wherein, when viewed in a sagittal cross sectional view, the medial articular surface of the anatomic patella component is non-conforming with the medial condyle surface of the femoral component.

2. The implantable orthopaedic knee prosthesis assembly of claim 1, wherein, when viewed in a sagittal cross sectional view, the lateral articular surface of the anatomic patella component defines a concave surface that conforms with a convex surface defined by the lateral condyle surface of the femoral component.

3. The implantable orthopaedic knee prosthesis assembly of claim 1, wherein, when viewed in a sagittal cross sectional view, the lateral articular surface of the dome patella component is non-conforming with the lateral condyle surface of the femoral component.

4. The implantable orthopaedic knee prosthesis assembly of claim 1, wherein, when viewed in a sagittal cross sectional view, both the lateral articular surface of the dome patella component and the lateral condyle surface of the femoral component define convex surfaces that are opposed to one another.

5. The implantable orthopaedic knee prosthesis assembly of claim 1, wherein, when viewed in a sagittal cross sectional view, both the medial articular surface of the anatomic patella component and the medial condyle surface of the femoral component define convex surfaces that are opposed to one another.

6. The implantable orthopaedic knee prosthesis assembly of claim 1, wherein, when viewed in a sagittal cross sectional view, the medial articular surface of the dome patella component is non-conforming with the medial condyle surface of the femoral component.

7. The implantable orthopaedic knee prosthesis assembly of claim 1, wherein, when viewed in a sagittal cross sectional view, both the medial articular surface of the dome patella component and the medial condyle surface of the femoral component define convex surfaces that are opposed to one another.

8. The implantable orthopaedic knee prosthesis assembly of claim 1, wherein each of the patella components comprises a monolithic polyethylene body.

* * * * *